United States Patent
Daley et al.

(10) Patent No.: US 8,440,632 B2
(45) Date of Patent: May 14, 2013

(54) PROTOPANAXADIOL-TYPE GINSENOSIDE COMPOSITIONS AND USES THEREOF

(75) Inventors: Thomas E. Daley, San Mateo, CA (US); Michael Tempesta, El Granada, CA (US)

(73) Assignee: Raptor Therapeutics Inc., Novato, CA (US)

( * ) Notice: Subject to any disclaimer, the term of this patent is extended or adjusted under 35 U.S.C. 154(b) by 177 days.

(21) Appl. No.: 12/863,979

(22) PCT Filed: Jan. 23, 2009

(86) PCT No.: PCT/US2009/000431
§ 371 (c)(1),
(2), (4) Date: Oct. 18, 2010

(87) PCT Pub. No.: WO2009/094177
PCT Pub. Date: Jul. 30, 2009

(65) Prior Publication Data
US 2011/0065659 A1    Mar. 17, 2011

Related U.S. Application Data

(60) Provisional application No. 61/023,310, filed on Jan. 24, 2008.

(51) Int. Cl.
*A61K 31/70* (2006.01)
*C07J 41/00* (2006.01)

(52) U.S. Cl.
USPC .................................................. 514/26; 536/5

(58) Field of Classification Search ......... 536/5; 514/26
See application file for complete search history.

(56) References Cited

U.S. PATENT DOCUMENTS

| | | | |
|---|---|---|---|
| 4,157,894 A | 6/1979 | Bombardelli | |
| 5,547,671 A | 8/1996 | Duthinh | |
| 6,759,397 B2 | 7/2004 | Jia | |
| 6,936,283 B2 | 8/2005 | Langeland | |
| 7,017,585 B2* | 3/2006 | Li et al. | 131/334 |
| 7,186,517 B2* | 3/2007 | Suva et al. | 435/7.21 |
| 2004/0009243 A1 | 1/2004 | Yun et al. | |

FOREIGN PATENT DOCUMENTS

| | | |
|---|---|---|
| CN | 1353992 A | 6/2002 |
| CN | 1698879 A | 11/2005 |
| KR | 10-2005-081247 A | 8/2005 |
| WO | WO 2005/016362 A1 | 2/2005 |
| WO | WO 2005/084392 A2 | 9/2005 |
| WO | WO 2005/116042 A1 | 12/2005 |

OTHER PUBLICATIONS

Bhatia et al, Cancer Letters, vol. 147, issues 1-2, Dec. 1, 1999, pp. 77-84.*
ISA/EP, International Search Report, dated May 18, 2009, for International Application No. PCT/US2009/000431.
ISA/EP, Written Opinion, dated May 18, 2009, for International Application No. PCT/US2009/000431.
ISA/EP. International Preliminary Report on Patentability, dated Aug. 5, 2010, for International Application No. PCT/US2009/000431.
Helms, 2004, "Cancer Prevention and Therapeutics: Panax Ginseng," *Alternative Medicine Review* 9(3):259-274.
Joo et al., 1977, "The Effect of Ginseng Saponins on Aldebyde Dehydrogenase," *Korean Biochem. J.* 10(2):109-120.
Kang et al., 1975, "Effect of Dietary Ginseng on the Ethanol Metabolism in Rats," *Korean Biochem J.* 8(3):189-195.
Kim et al., 1994, "Effect of Ginsenosides on Bovine Liver Mitochondria Aldehyde Dehydrogenase Activity," *Korean Journal of Gingseng Science* 18(1):10-16.
Lee et al., 1987, "Effects of Panax Ginseng on Blood Alcohol Clearance in Man." *Clinical and Experimental Pharmacology & Physiology* 14:543-546.
Lee et al., 1993, "Effect of Ginseng on Plasma Levels of Ethanol in the Rat," *Planta Medica* 59:17-19.
Petkov et al., 1977, "Accelerated Ethanol Elimination under the Effect of Ginseng (Experiments on Rats)," *Acta Physiologica et Pharmacologica Bulgarica* 3(1):46-50.
Visapaa et al., 2004 "Increased Cancer Risk in Heavy Drinkers with the Alcohol Dehydrogenase 1C*1 Allele, Possibly due to Salivary Acetaldehyde," *Gut* 53:871-876.
Yoon et al., 1993, "Cellular Distribution and Metabolism of Ginsenosides in Rat Liver," *Koryo Insam Hakhoechi* 17(2):114-122.
Yu et al., 2007, "Purification and Characterization of New Special Ginsenosidase Hydrolyzing Multi-Glycisides of Protopanaxadiol Ginsenosides, Ginsenosidase Type I," *Chem. Pharm. Bull.* 55(2):231-235.
Zhu et al., 2004, "Simultaneous Determination of Triterpene Saponins in Genseng Drugs by High-Performance Liquid Chromatography," *Chem. Pharm Bull* 52(8):995-998.
EPO Communication under Rule 71(3) EPC of Intent to Grant an European Patent, dated Jun. 28, 2012, for European Application No. EP 09704632.0, filed Jan. 23, 2009.
Yokoyama et al., "Alcohol-related cancers and aldehyde dehydrogenase-2 in Japanese alcoholics," Carcinogenesis 1998, 19(8), 1383-1387.
Yokoyama et al., "Genetic Polymorphisms of Alcohol and Aldehyde Dehydrogenases and Risk for Esophageal and Head and Neck Cancers," Jpn. J. Clin. Oncol. 2003, 33(3), 111-121.
Ohsawa et al., "Genetic deficiency of a mitochondrial aldehyde dehydrogenase increases serum lipid peroxides in community-dwelling females," J. Hum. Genet. 2003, 48, 404-409.

* cited by examiner

*Primary Examiner* — Elli Peselev
(74) *Attorney, Agent, or Firm* — Jones Day

(57) ABSTRACT

Provided herein are ginsenoside compositions comprising at least 10% (w/w) of a protopanaxadiol type of ginsenoside suitable for administration to a subject. Also provided are methods using the ginsenoside compositions for reducing acetaldehyde concentrations, preventing or ameliorating a symptom of elevated acetaldehyde concentration, or reducing the risk of diseases or disorders caused by the intake of ethyl alcohol.

24 Claims, 5 Drawing Sheets

PROTOPANAXADIOL-TYPE GINSENOSIDE COMPOSITIONS AND USES THEREOF

1. RELATED APPLICATIONS

Figure 1:
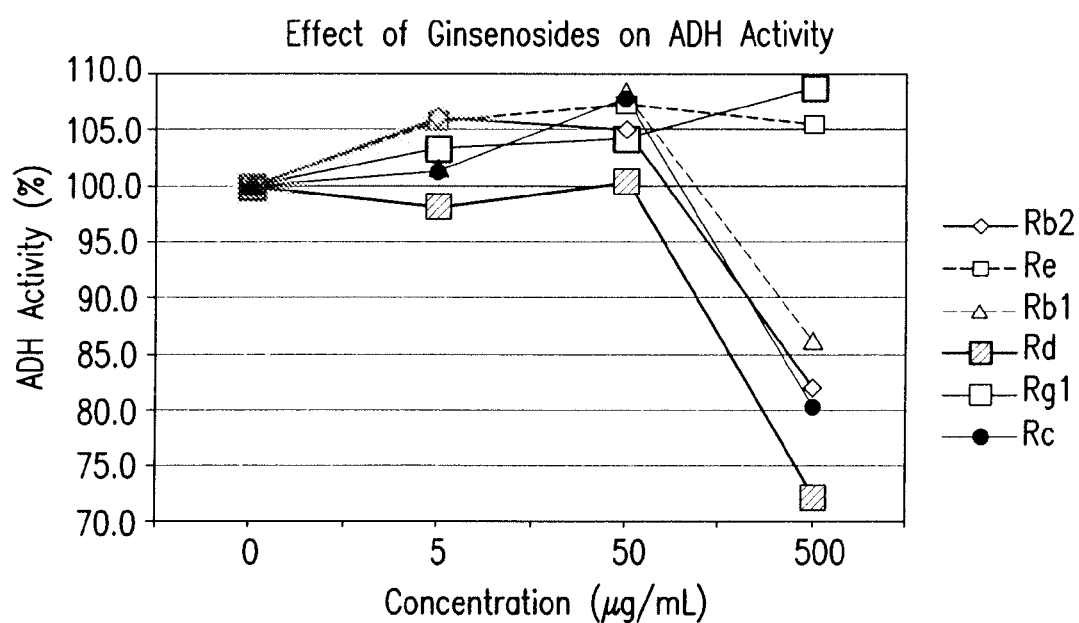

This application is a National Stage of International Application No. PCT/US2009/000431, filed Jan. 23, 2009, which claims the benefit of U.S. Provisional Application No. 61/023,310, filed Jan. 24, 2008, the contents of each of which applications are incorporated herein by reference in their entireties.

2. TECHNICAL FIELD

Provided herein are ginsenoside compositions and methods useful in reducing acetaldehyde concentrations, preventing or ameliorating a symptom of elevated acetaldehyde concentration, and reducing the risk of diseases or disorders caused by contact with an aldehyde, for example, from exposure to an aldehyde from an environmental source or from an aldehyde produced in vivo from ingestion of an alcohol.

3. BACKGROUND OF THE INVENTION

Aldehydes are chemically reactive substances having toxic effects in people and animals. Aldehydes are catalyzed into less reactive carboxylic acids via aldehyde dehydrogenase (ALDH), which are excreted from the body as such or as conjugates (Lindahl, *Crit. Rev. Biochem. Mol. Biol.* 1992, 27, 283-335). Multiple forms of ALDH exist including, for instance, cytosolic ALDH1A1 and mitochondrial ALDH1B1 and ALDH2, that catalyze a wide spectrum of aldehydes (Yoshida et al., *Eur. J. Biochem.* 1998, 251, 549-557; Vasiliou et al., *Pharmacogenetics* 1998; 9, 421-434).

Owing to its high affinity ($K_m$<5 µM) for acetaldehyde, ALDH2 is prominent among the dehydrogenases for the removal of acetaldehyde, which is, for example, the major aldehyde product of ethyl alcohol catabolism in people (Klyosov, *Biochemistry* 1996, 35, 4457-4467; Kurys et al., *J. Biol. Chem.* 1989, 264, 4715-4721). Acetaldehyde is linked to acute symptoms such as flushing, tachycardia, shortness of breath, dizziness, nausea, vomiting and headache as well as to long-term effects like increased risk of cancers of the upper digestive tract, breast cancer, liver disease, Alzheimer's disease, hypertension and myocardial infarction (see Visapaa et al., *Gut* 2004, 53, 871-876; Yokoyama et al., *Jpn. J. Clin. Oncol.* 2003, 33(3), 111-121; Ohsawa et al., *J. Hum. Genet.* 2003, 48, 404-409; and references cited therein). People with a variant ALDH2 (termed ALDH2*2 herein) having reduced activity on acetaldehyde catalysis exhibit alcohol-related sensitivity, e.g., facial flushing, tachycardia, etc., when drinking small portions of ethyl alcohol that would not normally elicit such reactions in carriers of the more prevalent ALDH2 isoform (Goedde et al., *Hum. Genet.* 1992, 88, 344-346; Xiao et al., *J. Clin. Invest.* 1995, 96, 2180-2186).

Exposure of the human population, particularly those in certain occupations, to acetaldehyde can be significant. For example, acetaldehyde is found in tobacco smoke and in automobile and diesel exhaust. It is also used or is generated in the manufacture of, for example, synthetic flavorings for processed foods, fumigants, and room air deodorizers. Combustion of wood, some plastics and some hard and soft polyurethane foams produce acetaldehyde (*Allyl Compounds, Aldehydes, Epoxides, and Peroxides*. IARC Monographs on the Evaluation of Carcinogenic Risk of Chemicals to Humans, vol. 36. Lyon, France: International Agency for Research on Cancer, 369 pp.).

Compositions and methods useful for assisting in maintaining low aldehyde levels in vivo would be advantageous for avoiding the undesirable and harmful effects of aldehydes, such as acetaldehyde.

*Ginseng* extracts are reported to have useful properties for treating cancer, enhancing the elimination of alcohol from blood, modulating alcohol dehydrogenase and ALDH activities, inter alia (see, e.g., Helms, *Alternative Medicine Review* 2004, 9(3), 259-274; Lee et al., *Clinical and Experimental Pharmacology & Physiology* 1987 14, 543-546; Joo et al., *Korean Biochem. J.* 1977, 10(2), 109-120). However, the active principals of the different *ginseng* plant species can include many different saponins, polysaccharides, flavonoids and volatile oils. For instance, over forty different *ginseng* saponins, termed ginsenosides, have been identified which are classified into various types including the protopanaxadiol (PPD), protopanaxatriol (PPT) and oleanonic acid types (see, e.g., Zhu et al., *Chem. Pham. Bull.* 2004, 52, 995-998 and Yu et al., *Chem. Pharm. Bull.* 2007, 55(2), 231-235, each of which is incorporated herein by reference in its entirety). Moreover, *ginseng* extracts vary considerably in their composition of active principals depending on various parameters such as age or type of root used and extraction method applied (see, e.g., U.S. Pat. No. 4,157,894).

4. SUMMARY OF THE INVENTION

In one aspect, ginsenoside compositions suitable for administration to a subject, for example, a human, are provided. The ginsenoside compositions can, for example, comprise one or more protopanaxadiol type of ginsenoside, such as ginsenoside Rb1, Rb2, Rb3, Rc, Rd, Rg3, Rh2, Rs1, Rs2, R1, R4, F2 and so forth.

In certain embodiments, the ginsenoside compositions suitable for administration to a human comprise at least 10% (w/w), at least 15% (w/w), at least 20% (w/w), at least 25% (w/w), at least 30% (w/w), at least 50% (w/w), at least 75% (w/w), at least 85% (w/w), at least 90% (w/w) or at least 95% (w/w) of one or more protopanaxadiol type of ginsenoside. In certain embodiments, the protopanaxadiol type of ginsenoside is ginsenoside Rb1, Rb2, Rb3, Rc, Rd, Rg3, Rh2, Rs1 or Rs2. In some embodiments, the protopanaxadiol type of ginsenoside is selected from Rb1, Rb2, Rc and Rd.

In certain embodiments, the ginsenoside composition consists essentially of one or more protopanaxadiol type of ginsenoside. In some embodiments, the ginsenoside composition consists essentially of ginsenoside Rb1, Rb2, Rc and/or Rd.

In some embodiments the ginsenoside composition is a nutraceutical composition.

In other embodiments the ginsenoside composition is a pharmaceutical composition.

In yet other embodiments the ginsenoside composition provided herein further comprises glutamine or silymarin.

In another aspect, provided herein are articles of manufacture comprising packaging material and a ginsenoside composition as described herein.

In one aspect, methods are provided herein, for example, for increasing the catalytic rate of ALDH to reduce aldehyde concentration in vivo, or as another example, for preventing, alleviating or ameliorating a symptom of elevated aldehyde concentration in vivo. The aldehyde can, for instance, be acetaldehyde.

In certain embodiments, methods are provided for increasing the rate of reducing acetaldehyde concentration in a subject comprising administering to a subject in need thereof an amount of a ginsenoside composition effective to increase the rate of reducing acetaldehyde concentration in the subject relative to the rate of reducing the acetaldehyde concentration in the subject in the absence of the ginsenoside composition.

In certain embodiments, methods are provided for preventing or ameliorating a symptom of elevated acetaldehyde concentration in a subject comprising administering to a subject in need thereof an amount of a ginsenoside composition effective to prevent or ameliorate a symptom of elevated acetaldehyde concentration in the subject. A symptom of elevated acetaldehyde can, for example, be a physiological symptom including acute symptoms such as, for example, flushing, elevated heart rate, palpitations, hypotension, nausea, dizziness, headache, vomiting, diarrhea, upset stomach, ataxia or confused consciousness as are or can be associated with alcohol consumption.

In some embodiments, methods are provided for reducing a likelihood or risk in a subject for a disease or disorder caused by exposure to acetaldehyde comprising administering to a subject in need thereof an amount of a ginsenoside composition effective to increase catabolism of acetaldehyde in the subject, thereby reducing a likelihood or risk in for a disease or disorder caused by exposure to acetaldehyde in the subject. For example, exposure to acetaldehyde can be a result of consuming ethyl alcohol. As another example, exposure to acetaldehyde can be a result of exposure to acetaldehyde in the environment outside of the subject.

In one aspect, provided herein are uses of a ginsenoside composition as provided herein for increasing the catalytic rate of ALDH to reduce aldehyde concentration in vivo, or as another example, for preventing, alleviating or ameliorating a symptom of elevated aldehyde concentration in vivo.

In certain embodiments, provided herein are uses of a ginsenoside composition as provided herein, for example, comprising at least 10% (w/w) of one or more of a protopanaxadiol type ginsenoside for the preparation of medicament for a) increasing the rate of reducing acetaldehyde concentration in a subject; b) preventing or ameliorating a symptom of elevated acetaldehyde concentration in a subject; or c) reducing a risk in a subject for a disease or disorder caused by intake of ethyl alcohol.

5. DESCRIPTION OF FIGURES

FIG. 1 provides a comparison of the effects of 5, 50 or 500 µg/mL of ginsenosides Rb2, Re, Rb1, Rd, Rg1 and Rc on alcohol dehydrogenase ("ADH") activity relative to ADH activity in the absence of ginsenoside ("0 µg/mL").

Figure 2:
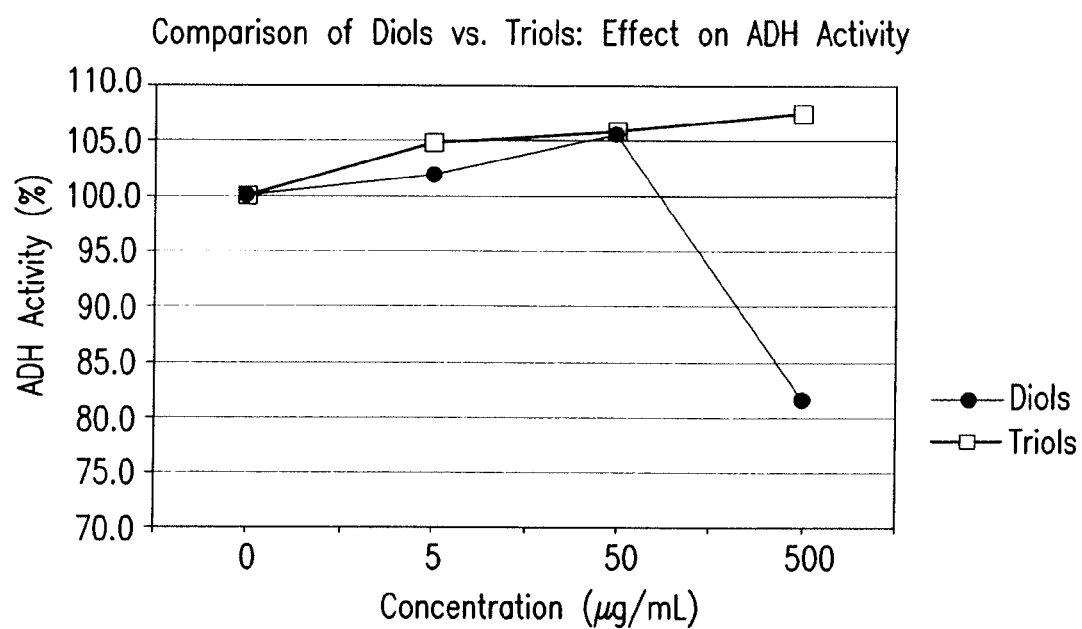

FIG. 2 provides a comparison of the average effect of protopanaxadiol type of ginsenosides Rb2, Rb1, Rd and Rc ("diols") versus protopanaxatriol type of ginsenosides Re and Rg1 ("triols") at 5, 50 or 500 µg/mL on ADH activity relative to ADH activity in the absence of ginsenoside ("0 µg/mL").

Figure 3:
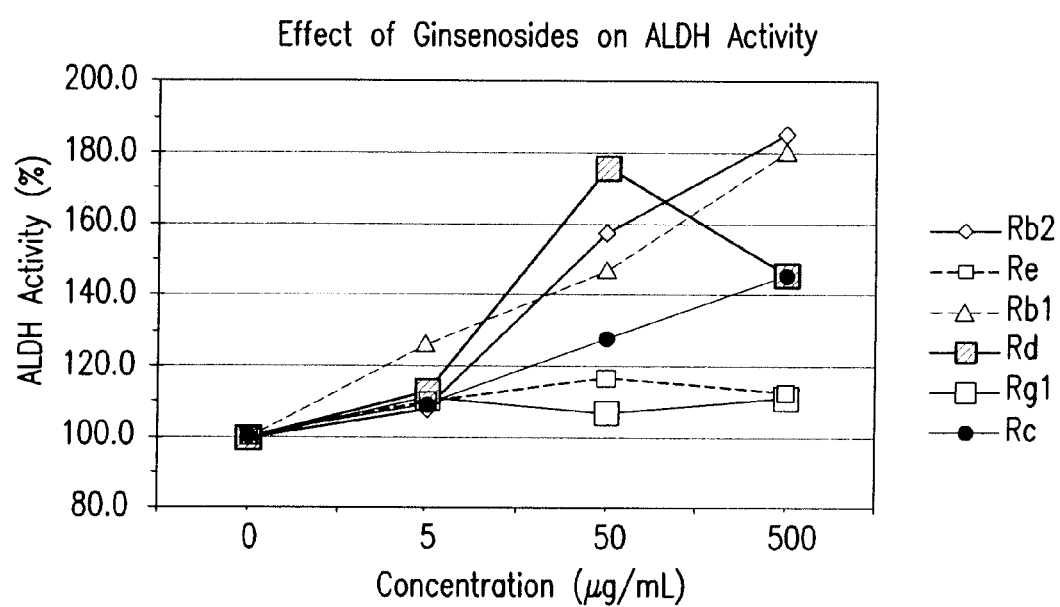

FIG. 3 provides a comparison of the effects of 5, 50 or 500 µg/mL of ginsenosides Rb2, Re, Rb1, Rd, Rg1 and Rc on aldehyde dehydrogenase ("ALDH") activity relative to ALDH activity in the absence of ginsenoside ("0 µg/mL").

Figure 4:
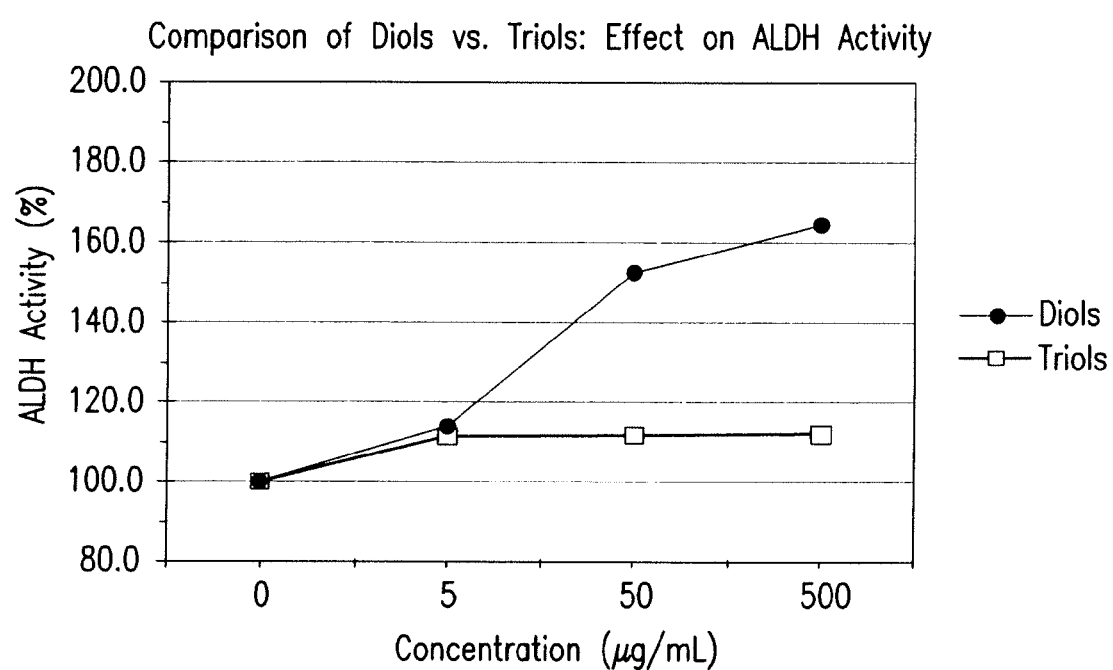

FIG. 4 provides a comparison of the average effect of protopanaxadiol type of ginsenosides Rb2, Rb1, Rd and Rc ("diols") versus protopanaxatriol type of ginsenosides Re and Rg1 ("triols") at 5, 50 or 500 µg/mL on ALDH activity relative to ALDH activity in the absence of ginsenoside ("0 µg/mL").

Figure 5A:
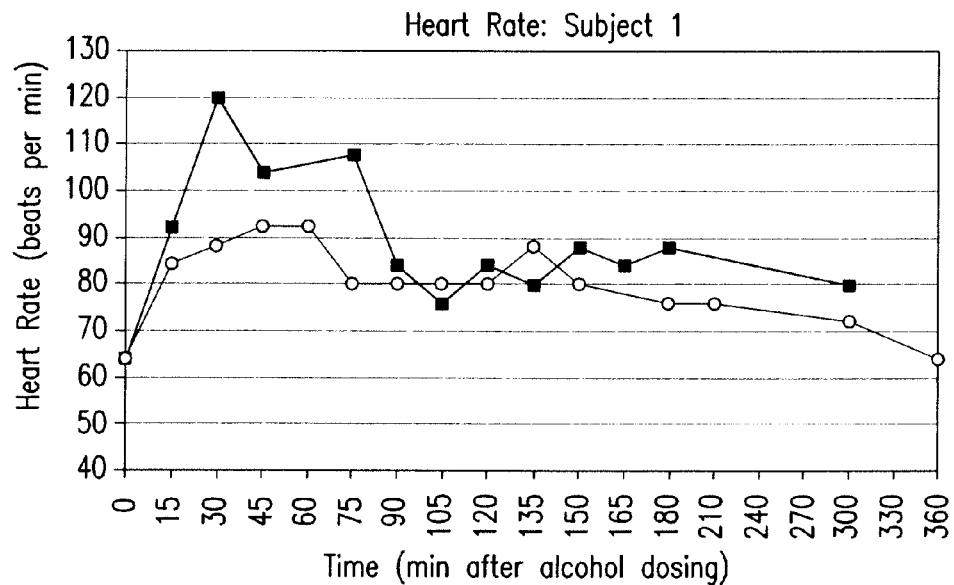
Figure 5B:
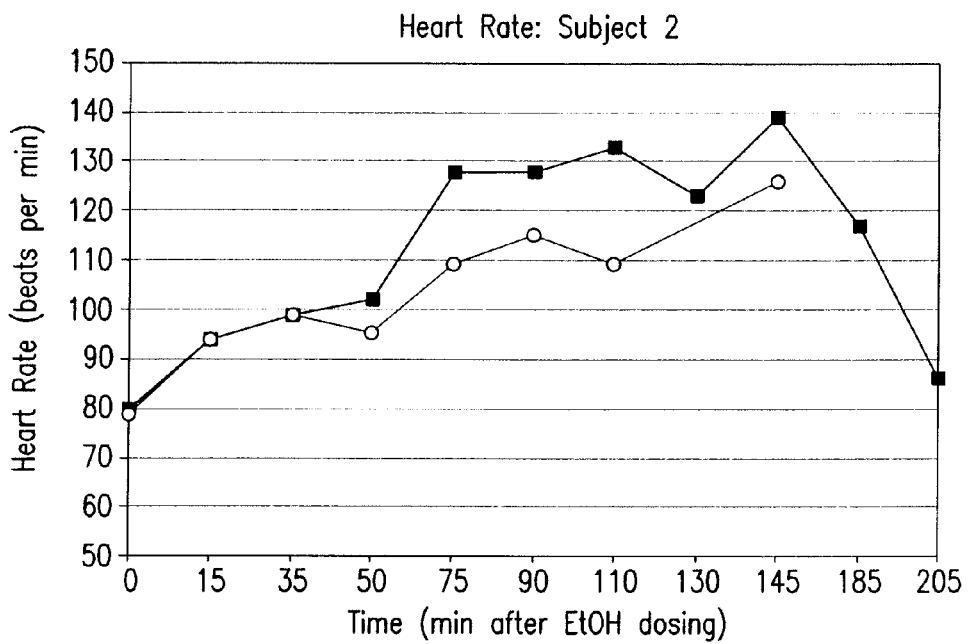

FIG. 5 provides heart rates of subject 1 (FIG. 5A) and subject 2 (FIG. 5B) over time after drinking ethyl alcohol under conditions where no ginsenoside composition has been consumed (solid squares) or after consuming a ginsenoside composition (circles).

6. TERMINOLOGY

Generally, the nomenclature used herein and the laboratory procedures in medicinal chemistry, biochemistry, and pharmacology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

The term "about" as used herein refers to a value that is no more than 10% above or below the value being modified by the term. For example, the term "about 5%" means a range from 4.5% to 5.5%.

The term "subject" refers to animals such as mammals, including, but not limited to, primates (e.g., humans), monkeys, cattle, sheep, goats, horses, dogs, cats, rabbits, pigs, deer, bear, rats, mice and the like. In preferred embodiments, the subject is a human.

The terms "treat," "treating" or "treatment," as used herein, refers to a method of alleviating or abrogating a disorder and/or its attendant symptoms.

The terms "prevent," "preventing" or "prevention," in certain embodiments, refer to a method of barring a subject from acquiring a disorder and/or its attendant symptoms. In certain embodiments, the terms "prevent," "preventing," or "prevention," refer to a method of reducing the likelihood or risk of a subject acquiring a disorder and/or its attendant symptoms.

As used herein, the term "pharmaceutically acceptable" means approved by a regulatory agency of the Federal or a state government or listed in the U.S. Pharmacopeia or other generally recognized pharmacopeia for use in animals, and more particularly in humans. "Pharmaceutically acceptable carrier," and "pharmaceutically acceptable excipient" refer to a pharmaceutically-acceptable material, composition, or vehicle, such as a liquid or solid filler, diluent, excipient, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy*, 21st Edition; Lippincott Williams & Wilkins: Philadelphia, Pa., 2005; *Handbook of Pharmaceutical Excipients*, 5th Edition; Rowe et al., Eds., The Pharmaceutical Press and the American Pharmaceutical Association: 2005; and *Handbook of Pharmaceutical Additives*, 3rd Edition; Ash and Ash Eds., Gower Publishing Company: 2007; *Pharmaceutical Preformulation and Formulation*, Gibson Ed., CRC Press LLC: Boca Raton, Fla., 2004).

As used herein, the term "composition" is meant to include, for example, dietary supplements, food additives, nutraceuticals, pharmaceutical compositions and physiologically acceptable compositions and so forth. It will be understood that where a ginsenoside (for example, ginsenoside Rb1, Rb2, Rc and/or Rd) in a "composition" also occurs in a natural source, the term "composition" does not include the natural source of the component, but can, in certain embodiments, encompass a physically or chemically modified or processed form of the natural source, such as an extract of the natural source.

The term "effective amount" as used herein refers to the amount of ginsenoside composition that is sufficient to produce a desirable or beneficial effect when contacted for example to an aldehyde dehydrogenase enzyme, or, as another example, when administered to a subject. In certain embodiments the "effective amount" of a ginsenoside composition is, e.g., the amount to increase the rate that acetaldehyde concentration is reduced in a subject compared to the rate that acetaldehyde concentration is reduced in the absence of the ginsenoside composition. In some embodiments, the "effective amount" is, e.g., the amount to prevent or ameliorate a symptom of elevated acetaldehyde concentration in a subject, or to reduce the likelihood or risk in a subject for a disease or disorder caused by acetaldehyde exposure.

The term "symptom" as used herein is interchangeable with "sign". Therefore, as used herein "symptom" refers to a physical condition which indicates a particular illness or disorder (e.g., Longman Dictionary of Contemporary English (1995). Third edition) detectable by the subject suffering from a particular disease or disorder or detectable by a person other than the subject without verbal information from said subject.

The terms "compromised aldehyde dehydrogenase," or "compromised ALDH2," are intended to mean that a subject has an ALDH2 enzyme that exhibits less activity than the ALDH2 enzyme most commonly found in the human population. The enzymatic activity of ALDH2 can be determined by, e.g., the aldehyde dehydrogenase activity assay as described in Xiao et al., *J. Clin. Invest.* 1995, 96, 2180-2186. As used herein, a subject with "compromised aldehyde dehydrogenase" or "compromised ALDH2," may, for example, include those who are a homozygous or heterozygous carrier of the variant ALDH2 allele of the ALDH2 gene described in Goedde et al., *Hum. Genet.* 1992, 88, 344-346 and Xiao et al., *J. Clin. Invest.* 1995, 96, 2180-2186, incorporated herein by reference in their entireties.

7. DETAILED DESCRIPTION OF THE INVENTION

In one aspect, provided herein are compositions comprising one or more protopanaxadiol type of ginsenoside, for example, ginsenoside Rb1, Rb2, Rb3, Rc, Rd, Rg3, Rh2, Rs1, Rs2, R1, R4, F2 and so forth, suitable for administration to a subject. In some embodiments, the composition provided consists essentially of a protopanaxadiol type of ginsenoside. In certain embodiments, the composition provided consists essentially of ginsenoside Rb1, Rb2, Rc and/or Rd.

Without intending to be bound by any particular theory or limitation, it is believed that protopanaxadiol type of ginsenosides, but generally not, for example, protopanaxatriol ginsenosides, increase the activity of aldehyde dehydrogenase (ALDH). As such, without intending to be bound by any particular theory or limitation, the ginsenoside compositions provided herein are believed to increase the rate that aldehyde levels would be otherwise reduced in vivo.

In certain embodiments, provided herein are ginsenoside compositions suitable for administration to a human comprising at least 10% (w/w), at least 15% (w/w), at least 20% (w/w), at least 25% (w/w), at least 30% (w/w), at least 50% (w/w), at least 75% (w/w), at least 85% (w/w), at least 90% (w/w) or at least 95% (w/w) of one or more protopanaxadiol type of ginsenoside. In certain embodiments, the one or more protopanaxadiol type of ginsenoside are selected from the group consisting of ginsenoside Rb1, Rb2, Rb3, Rc, Rd, Rg3, Rh2, Rs1 and Rs2. In some embodiments, the one or more protopanaxadiol type of ginsenoside are selected from Rb1, Rb2, Rc and Rd.

In some embodiments, compositions are provided where the ratio of protopanaxadiol type of ginsenoside to protopanaxatriol type of ginsenosides is from about 100:0 to 25:27 or from about 75:25 to about 50:60. In certain embodiments of the ginsenoside compositions provided, the ratio of protopanaxadiol type of ginsenoside to protopanaxatriol type is about 90:10, about 80:20 or about 60:40.

In certain embodiments, the ginsenoside composition consists of a non-ginsenoside fraction and a ginsenoside fraction, wherein the ginsenoside fraction comprises at least 10, 15, 20, 25, 30, 50, 75 or 95% (w/w) of a protopanaxadiol type of ginsenoside, for instance, one or more of Rb1, Rb2, Rc and Rd. In certain embodiments, the ginsenoside fraction consists of a protopanaxadiol type of ginsenoside, for instance, one or more of Rb1, Rb2, Rc and Rd. The non-ginsenoside fraction can, for example, include one or more excipients, vehicles, nutraceuticals, foodstuffs, vitamins, minerals, dietary supplements, and so forth, to the extent that such components do not include a ginsenoside.

The chemical structures of ginsenosides, including protopanaxadiol type of ginsenosides such as ginsenosides Rb1, Rb2, Rc and Rd, are known to those of skill in the art (see, e.g., Yu et al., *Chem. Pharm. Bull.* 2007, 55(2), 231-235; Court, "The Principal Active Chemicals in *Panax* species" in *Ginseng: The Genus Panax* (Court, ed., Harwood Academic Publishers, Amsterdam, The Netherlands, 2000), both of which are incorporated herein by reference in their entireties). Protopanaxadiol type ginsenosides can be obtained by any method known in the art including, for example, by purification from natural plant sources, for example, *ginseng* including *Panax ginseng* (Asian or Korean *ginseng*) and *Panax quinquefolius* (American *ginseng*), and cultured plant sources including *ginseng* cultures (see, e.g., *Ginseng: The Genus Panax* (Court, ed., Harwood Academic Publishers, Amsterdam, The Netherlands, 2000) and citations cited therein; Yua et al., *Biochemical Engineering Journal* 2002, 11, 211-215, each of which is incorporated herein by reference). Ginsenosides including ginsenoside Rb1, Rb2, Rc and Rd are also commercially available from vendors such as ChromaDex Inc., Irvine, Calif., USA, Wako Pure Chemical Industries, Ltd., Osaka, Japan and Sigma-Aldrich, St. Louis, Mo. USA.

For example, procedures for obtaining ginsenosides Rb1, Rb2, Rc and/or Rd typically comprise aqueous or organic extraction of one or more suitable *Panax* species, evaporating the extracted solution to dryness, followed by column chromatography, thin-layer chromatography, and/or high performance chromatography to obtain a purified ginsenoside fraction. Techniques for the extraction and purification of plant extracts are known to the skilled artisan, and may be adapted for the preparation of each of or a mixture of one or more of Rb1, Rb2, Rc, or Rd, from techniques such as the ones disclosed in the following documents: U.S. Pat. No. 6,156,291; U.S. Pat. No. 6,083,932; U.S. Pat. No. 4,157,894; U.S. Pat. No. 5,137,878; and U.S. Pat. No. 5,230,889, each of which is incorporated herein by reference. Isolation and purification procedures for Rb1, Rb2, Rc and Rd are also described in, for example, Shibata et al., *Economic and Medicinal Plant Research*, World Scientific, Philadelphia, pp. 217-284, 1985; U.S. Pat. No. 7,235,267; Kawashima et al., *J. Med. Pharmacol. Soc. Wakan-Yaku* 1986, 3, 235-236; and Oura et al., *Journal of Biochemistry (Tokyo)* 1975, 77(5), 1057-65, each of which is hereby incorporated by reference.

In various embodiments, depending on the intended use and without limitation, a composition as provided herein can be in the form of a dietary supplement or nutraceutical. For example, in certain embodiments, a dietary supplement or nutraceutical is provided comprising or consisting essentially of a protopanaxadiol type of ginsenoside. In certain embodiments, the dietary supplement or nutraceutical comprises or consists essentially of one or more of ginsenoside Rb1, Rb2, Rb3, Rc, Rd, Rg3, Rh2, Rs1 and/or Rs2. In some embodiments, the dietary supplement or nutraceutical comprises or consists essentially of one or more of ginsenoside Rb1, Rb2, Rc and/or Rd.

Generally, a dietary supplement is consumed by a subject independent of any food composition, unlike a food additive which is incorporated into a food composition during the processing, manufacture, preparation, or delivery of the food composition, or just before its consumption. A dietary supplement provides, in addition to nutrition, a therapeutic or prophylactic function to the consumer. A "nutraceutical," as used herein refers to a product prepared, isolated or purified from a natural source, such as a plant or plant product, not usually associated with food, for instance an *Panax ginseng* type root, intended to be administered to a subject to have physiological benefit or to prevent or ameliorate a condition or disorder in the subject, that is, the nutraceutical provides a benefit other than a nutritional benefit, if any.

In various embodiments, the composition of the invention typically comprises one or more consumable fillers or carriers. The term "consumable" means the filler or carrier that is generally suitable for, or is approved by a regulatory agency of the Federal or a state government, for consumption by animals, and more particularly by humans. In certain embodiments, the meaning of the term "dietary supplement" or "nutraceutical" is the meaning of those terms as defined by a regulatory agency of the Federal or a state government, including the United States Food and Drug Administration.

As provided herein, the dietary supplement or nutraceutical can be used to reduce aldehyde, for example, acetaldehyde, concentration in a subject comprising administering to the subject in need thereof an amount of the ginsenoside in the dietary supplement or nutraceutical effective to reduce the aldehyde concentration in the subject.

As also provided herein, the dietary supplement or nutraceutical can be used to prevent or ameliorate a symptom of elevated aldehyde, for example, acetaldehyde, concentration in a subject comprising administering to a subject in need thereof an amount of the ginsenoside in the dietary supplement or nutraceutical effective to prevent or ameliorate a symptom of elevated aldehyde concentration in the subject.

In certain embodiments, the dietary supplement or nutraceutical can be used to reduce the risk in a subject for a disease or disorder caused by intake of ethyl alcohol comprising administering to a subject in need thereof an amount of the ginsenoside in the dietary supplement or nutraceutical effective to increase catabolism of acetaldehyde in the subject, wherein acetaldehyde is a product of ethyl alcohol consumption by the subject and wherein increasing catabolism of acetaldehyde reduces a risk for a disease or disorder in the subject caused by intake of the ethyl alcohol.

Typically, a dietary supplement or nutraceutical as provided herein is intended to be orally taken or consumed. The dietary supplement or nutraceutical can be in a solid form or a liquid form.

For example, a composition as provided herein, such as a dietary supplement or nutraceutical, can be a reconstitutable powder that, when reconstituted with a liquid, such as drinking water, can provide a beverage. In another embodiment, a composition as provided herein can be incorporated into other foodstuff, such as but not limited to cooking oil, frying oil, salad oil, margarine, mayonnaise or peanut butter. Oils containing the compounds of the invention can be emulsified and used in a variety of water-based foodstuffs, such as drinks. Accordingly, in one embodiment, compositions of the invention can be a beverage, such as but not limited to fortified mineral water, fortified distilled water, a fruit juice-based beverage, a shake, a milk-based beverage, a dairy product-based beverage, a yoghurt-based beverage, a carbonated water-based beverage, an alcoholic drink, a coffee-based beverage, a green tea-based beverage, a black tea-based beverage, a grain-based beverage, a soybean-based beverage, or a beverage based on plant extracts.

In addition to beverages, the compositions of the present invention may be combined with other foodstuff, for example, syrups, starches, grains, or grain flour.

In one embodiment the ginsenoside composition provided herein is suitable for oral administration to a subject.

In an additional embodiment the ginsenoside composition provided herein is a nutraceutical composition and further comprises a physiologically acceptable carrier, excipient, diluent or solvent.

In certain embodiments, provided herein are compositions, wherein the ginsenoside composition, as described above, is a pharmaceutical composition and further comprises a pharmaceutical acceptable carrier, excipient, diluent or solvent.

Pharmaceutical carriers, excipients, diluents or solvents can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Examples of suitable pharmaceutical carriers are described in *Remington: Science and Practice of Pharmacy*, 21$^{st}$ ed., Lippincott Williams & Wilkins, Philadelphia Pa. (2005) and *Ansel's Pharmaceutical Dosage Forms and Drug Delivery Systems*, 8$^{th}$ ed., Lippincott Williams & Wilkins, Philadelphia Pa. (2004).

Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition depends on a variety of factors well known in the art including, but not limited to, the way in which the dosage form will be administered to a patient and the specific active ingredients in the dosage form. The pharmaceutical composition, if desired, can also contain minor amounts of wetting or emulsifying agents, or pH buffering agents.

The compositions provided herein, can, for example, encompass anhydrous pharmaceutical compositions and dosage forms comprising active ingredients, since water can facilitate the degradation of some compounds.

A pharmaceutical composition, as provided herein, is formulated to be compatible with its intended route of administration. Examples of routes of administration include, but are not limited to, parenteral, e.g., intravenous, intradermal, subcutaneous, oral (e.g., inhalation), intranasal, and transdermal (topical) administration. In a specific embodiment, the composition is formulated in accordance with routine procedures as a pharmaceutical composition adapted for intravenous, subcutaneous, intramuscular, oral, intranasal or topical administration to subjects. In a preferred embodiment, a pharmaceutical composition is formulated in accordance with routine procedures for oral administration to humans. Typically, compositions for intravenous administration are solutions in sterile isotonic aqueous buffer. Where necessary, the composition may also include a solubilizing agent and a local anesthetic such as lidocaine to ease pain at the site of the injection. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

Generally, the ingredients of pharmaceutical compositions as provided herein are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In certain embodiments, the ginsenoside composition, including pharmaceutical or nutraceutical compositions comprising the ginsenoside composition, can be in a sustained-release formulation. Suitable examples of sustained-release formulations include, for example, semipermeable matrices of solid hydrophobic polymers containing the ginsenoside composition provided herein, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

In some embodiments, the compositions as provided herein can be in a unit dosage form. A unit dosage form can, for example, be a nutraceutical composition or a pharmaceutical composition. Unit dosage forms of the invention comprise a prophylactically or therapeutically effective amount of a ginsenoside composition, as described hereinabove, and typically one or more consumable and/or physiologically or pharmaceutically acceptable carriers or excipients, as described above.

In certain other embodiments, unit dosage forms comprise an amount of ginsenoside composition, effective to reduce acetaldehyde concentration in a subject, effective to prevent or ameliorate a symptom of elevated acetaldehyde concentration in a subject, or effective to reduce a risk in a subject for a disease or disorder caused by intake of ethyl alcohol.

Further provided herein are unit forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Different effective amounts may be applicable for different conditions. Unit dosage forms can, for example, take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent preferably in purified form, together with a suitable amount of carrier so as to provide the form for proper administration to the patient. The formulation should suit the mode of administration. In a preferred embodiment, the unit dosage forms are sterile and in suitable form for administration to a subject, preferably a human.

The composition, shape, and type of dosage forms of the invention will typically vary depending on their use. For example, the prophylactically and therapeutically effective dosage form may vary among different types of diseases. Similarly, a parenteral dosage form may contain smaller amounts of ginsenoside composition than an oral dosage form used to treat the same disease or disorder. These and other ways in which specific dosage forms encompassed by this invention will vary from one another will be readily apparent to those skilled in the art. See, e.g., *Remington: Science and Practice of Pharmacy*, $21^{st}$ ed., Lippincott Williams & Wilkins, Philadelphia Pa. (2005); *Ansel's Pharmaceutical Dosage Forms and Drug Delivery Systems*, $8^{th}$ ed., Lippincott Williams & Wilkins, Philadelphia Pa. (2004).

In one embodiment, the unit dosage form is a container, preferably a sterile container, containing an effective amount of ginsenoside composition and a pharmaceutically acceptable carrier or excipient.

In some embodiments, an article of manufacture is provided that can simplify the administration of ginsenoside compositions to a subject. A typical article of manufacture of the invention comprises a unit dosage form of ginsenoside compositions.

In one embodiment the article of manufacture comprises packaging material and a ginsenoside composition, wherein said composition is a pharmaceutical composition or nutraceutical composition as described herein.

The article of manufacture can further comprise a label or printed instructions regarding the use of the composition or other informational material that advises the dietitian, physician, technician, consumer, subject, or patient on how to appropriately increase the reduction of aldehyde concentration in a subject, prevent or ameliorate a symptom of elevated aldehyde concentration in a subject, or reduce a likelihood or risk for a disease or disorder in a subject caused by contact with an aldehyde, for example due to exposure to the aldehyde in the environment or due to production of the aldehyde in vivo from the intake of an alcohol. In other words, the article of manufacture includes instruction means indicating or suggesting a dosing regimen including, but not limited to, actual doses, monitoring procedures, and other monitoring information.

As with any pharmaceutical product, dietary supplement or nutraceutical, the packaging material and container included in the article of manufacture are designed to protect the stability of the product during storage and shipment.

Article of manufacture of the invention can further comprise devices that are useful for administering the unit dosage forms. Examples of such devices include, but are not limited to, syringes, drip bags, patches, and inhalers.

Compositions as provided herein can, for example, be suitable for oral administration, and orally consumable compositions including but not limited to dietary supplements or nutraceutical compositions of the invention, can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington: Science and Practice of Pharmacy*, $21^{st}$ ed., Lippincott Williams & Wilkins, Philadelphia Pa. (2005); *Ansel's Pharmaceutical Dosage Forms and Drug Delivery Systems*, $8^{th}$ ed., Lippincott Williams & Wilkins, Philadelphia Pa. (2004).

In yet other embodiments, compositions as provided herein can comprise one or more protopanaxadiol-type ginsenoside in combination with one or more active agents. Exemplary active agents can include, for example, a vitamin, an antioxidant, an anti-inflammatory agent, a non-steroid anti-inflammatory agent, an anti-histamine and the like. In certain embodiments, a combination composition comprises one or more protopanaxadiol-type ginsenoside in combination with glutamine or silymarin (flavonoid complex of *Slybum marianum* or milk thistle). In certain embodiments, a combination composition comprises one or more protopanaxadiol-type ginsenoside in combination with aspirin or ibuprofen.

In certain embodiments, combination compositions comprising a protopanaxadiol-type ginsenoside and glutamine or silymarin or both glutamine and silymarin, can be in a unit dosage form. For example, a combination composition in unit dosage form can comprise about 5 mg to about 500 mg protopanaxadiol type ginsenoside, about 50 mg to about 3 g glutamine and/or about 20 mg to about 800 mg silymarin. Such unit dosage forms optionally can further comprise one or more diluent, carrier, vehicle, stabilizer, flavoring, or other component known to those of skill in the art for inclusion into unit dosage forms when preparing, for instance, nutraceutical or pharmaceutical compositions.

In one aspect, methods are provided herein for use of a ginsenoside including the ginsenoside compositions as described above.

In certain embodiments, the methods provided comprise administering a ginsenoside to a subject. The ginsenoside can be any ginsenoside, or combination of ginsenosides, known in the art. For example, in the methods provided, the ginsenoside can one or more of a protopanaxadiol type, protopanaxatriol type, oleanane type and/or other types, as described, for instance, in Court, "The Principal Active Chemicals in *Panax* species" in *Ginseng: The Genus Panax* (Court, ed., Harwood Academic Publishers, Amsterdam, The Netherlands, 2000), incorporated herein by reference in its entirety.

In some embodiments, the ginsenoside is a protopanaxadiol type of ginsenoside, such as, for example, Rb1, Rb2, Rb3, Rc, Rd, Rg3, Rh2, Rs1 and/or Rs2. In certain embodiments, the ginsenoside is one or more of ginsenoside Rb1, Rb2, Rc and Rd.

The ginsenoside can, for example, be administered as a pure or highly purified ginsenoside or mixture of ginsenosides, or as a composition thereof, for example, comprising a carrier, diluent, vehicle and/or excipient and the like, or nutraceutical, pharmaceutical or other composition as described above.

In certain embodiments, methods are provided for the increased reduction of an aldehyde concentration in a subject comprising administering to a subject in need thereof an amount of a ginsenoside effective to increase reduction the aldehyde concentration in the subject relative to a condition where the subject is not administered the ginsenoside. In some embodiments, the aldehyde is acetaldehyde.

It will be understood that the source of aldehyde in the subject can be due to any source or factor, for example, exposure or contact to aldehyde present in the environment outside of the subject, or, for example, aldehyde that is produced metabolically in the subject due to intake (by, for example, ingestion, transdermal crossing, inhalation, etc.) of an alcohol.

For instance, in certain embodiments, the aldehyde is acetaldehyde produced in vivo due to consumption of ethyl alcohol. In some embodiments the aldehyde is produced in vivo due to ingestion of methanol, anti-freeze, ethylene glycol, or other alcohol.

In some embodiments, methods are provided for reducing an aldehyde concentration in a subject comprising administering to a subject in need thereof an amount of a ginsenoside effective to reduce the aldehyde concentration in the subject.

As demonstrated in the examples below, and without intending to be limited by any theory or mechanism, protopanaxadiol type of ginsenosides increase the activity of aldehyde dehydrogenase (ALDH). Since aldehyde dehydrogenases are typically present in a subject, phrases used herein in conjunction with the methods provided for use of a ginsenoside such as "reduce an aldehyde concentration in a subject" and the like, can, for instance, mean increasing the rate at which an aldehyde is reduced in a subject. Moreover, as demonstrated in the examples provided herein, and without intending to be limited by any theory or mechanism, protopanaxadiol type of ginsenosides decrease activity of alcohol dehydrogenases. Since alcohol dehydrogenases are typically present in a subject to catalyze alcohols into aldehydes, phrases used herein in conjunction with the methods provided for use of a ginsenoside such as "reduce an aldehyde concentration in a subject" and similar phrases, can, for instance, mean prevent or reduce an aldehyde concentration in a subject that would otherwise occur in the absence of the ginsenoside being administered to the subject. It will also be understood, that without intent to be limited to any particular theory or limitation, that protopanaxadiol type of ginsenosides administered to a subject may both decrease alcohol dehydrogenase activities and increase aldehyde dehydrogenase activities in the subject.

In some embodiments, methods are provided for preventing or ameliorating a symptom of elevated acetaldehyde concentration in a subject comprising administering to a subject in need thereof an amount of a ginsenoside effective to prevent or ameliorate a symptom of elevated acetaldehyde concentration in the subject.

In yet other embodiments, provided herein are methods for reducing a likelihood or risk in a subject for a disease or disorder caused by intake of ethyl alcohol comprising administering to a subject in need thereof an amount of a ginsenoside effective to increase catabolism of acetaldehyde in the subject. The acetaldehyde can, for example, be a product of ethyl alcohol consumption by the subject wherein increasing catabolism of acetaldehyde reduces the likelihood or risk for a disease or disorder caused by the subject's intake of the ethyl alcohol.

In certain embodiments of the methods provided herein, the subject is human. In certain embodiments the subject has an altered ethyl alcohol metabolism. For example, in some embodiments, the subject has a reduced aldehyde dehydrogenase subtype 2 (ALDH2) activity. In other embodiments, the subject is a homozygous or heterozygous carrier of the ALDH2*2 allele, as discussed above.

In certain embodiments, methods are provided for increasing the catabolism of acetaldehyde in a subject, thereby reducing acetaldehyde concentrations in the subject.

As such, it will be understood that such methods can, for example, be utilized for alleviating discomfort of the acute symptoms of acetaldehyde (such as, for example, dizziness, tachycardia, flushing, headache, and so forth).

The methods provided herein can, for example, also be advantageously to minimize exposure to acetaldehyde concentrations and thereby reduce the likelihood or risk of developing a disease or disorder associated with the long-term exposure to acetaldehyde.

Acetaldehyde exposure can, for example, arise as a result of ethyl alcohol consumption. In some embodiments, acetaldehyde is a product of such as, but not limited to, cigarette smoke or exposure to acetaldehyde in the environment outside of the subject.

In certain embodiments, a symptom of elevated acetaldehyde concentration comprises flushing, elevated heart rate, palpitations, hypotension, nausea, dizziness, headache, vomiting, diarrhea, upset stomach, ataxia or confused consciousness.

In certain embodiments, the disease or disorder comprises hangover, alcoholic gastritis or alcohol-induced liver damage.

In certain embodiments, the disease or disorder comprises upper aerodigestive tract cancers, digestive tract cancers or breast cancer. In an additional embodiment the upper aerodigestive tract cancer comprises esophageal, oropharynx, hypopharynx, larynx, head or neck cancer. In a further embodiment the digestive cancer comprises stomach or colon cancer.

In certain embodiments, the disease or disorder comprises late-onset Alzheimer's disease, hypertension, myocardial infarction, Parkinson's disease, amyotropic lateral sclerosis, and cerebral ischemia.

In certain embodiments, the acetaldehyde concentration is in the blood, salvia and/or tissue of the subject.

In certain embodiments, the methods provided herein reduce the concentration of any aldehyde that can be a substrate of ALDH2 in a subject comprising administering to a subject in need thereof an amount of a ginsenoside effective to reduce the concentration of said aldehyde in the subject.

In certain embodiments, the methods provided herein prevent or ameliorate a symptom of elevated aldehyde concentration in a subject, wherein said aldehyde is a substrate of ALDH2, comprising administering to a subject in need thereof an amount of a ginsenoside effective to prevent or ameliorate a symptom of elevated aldehyde concentration in the subject.

In certain embodiments, methods for increasing the activity of ALDH2 in a subject comprising administering an amount of ginsenoside effective to increase the activity of ALDH2 in the subject are provided.

In certain embodiments, methods for decreasing the activity of an alcohol dehydrogenase are provided. For example, in some embodiments, a method can comprise administering to a subject an amount of ginsenoside effective to decrease the activity of an alcohol dehydrogenase in the subject.

In some embodiments, methods are provided comprising administering to a subject an amount of ginsenoside effective to increase an ALDH activity and decrease an alcohol dehydrogenase activity.

In yet other embodiments, methods are provided related to animal health. Toxicity associated from drinking alcohols including those in antifreeze can be lethal even fatal to animals. For example, in some embodiments, methods are provided comprising administering a ginsenoside to an animal in an amount effect to increase ALDH activities in the animal, decrease alcohol dehydrogenase activities in the animal, or both increase ALDH activity and decrease alcohol dehydrogenase activities in the animal. Such methods can, for example, alleviate a symptom of an alcohol in an animal. Alcohols can include methanol, ethyl alcohol, ethylene glycol, butanol, isopropyl alcohol, and the like. In some embodiments, the methods provided increase the rate of reducing an aldehyde in an animal. In some embodiments, the methods prevent or to reduce the catalysis of an alcohol to aldehyde in an animal.

In certain embodiments the animal is a mammal. In some embodiments the animal is a companion, domesticated, research or farm animal (e.g., dogs, rabbits, rats, mice, guinea pigs, cats, pigs, sheep, goats, horses, cattle and the like) or wild animal (e.g, monkeys, bears, deer, seals, otters and so forth).

The amount of ginsenoside administered in the methods provided above that will be effective, for example, for the increased reduction of aldehyde concentration, prevention or amelioration of a symptom of elevated aldehyde concentration, or reducing a likelihood or risk for a disease or disorder caused by intake of an alcohol, in the subject will vary with the nature and severity of the exposure to the aldehyde and the route by which the ginsenoside is administered. Frequency and dosage will also vary according to factors specific for each subject or patient such as age, weight, response, and the past medical history of the patient. Effective doses may be extrapolated from dose-response curves derived from in vitro or animal model test systems. Suitable regiments can be selected by one skilled in the art by considering such factors and by following, for example, dosages reported in the literature and recommended in the *Physician's Desk Reference* (57th ed., 2003).

Exemplary doses of ginsenoside in the methods provided herein include milligram or microgram amounts of total ginsenoside per kilogram of subject weight (e.g., about 1 microgram per kilogram to about 100 milligrams per kilogram, about 100 micrograms per kilogram to about 5 milligrams per kilogram, or about 1 microgram per kilogram to about 50 micrograms per kilogram). Generally, the daily dose range of a ginsenoside described herein lie with the range of from about 0.01 mg of total ginsenoside to about 1000 mg per day. These amounts can, for example, be given as a single once-a-day dose or as divided doses throughout a day. In one embodiment, the daily dose is administered twice daily in equally divided doses. More typically, doses of the ginsenoside will be administered prior to an expected exposure to an aldehyde, or after exposure to the aldehyde is apparent, for example, by manifestation of the acute symptoms of aldehyde exposure in the subject.

Specifically, a daily dose range should be from about 5 mg to about 500 mg per day, more specifically, between about 10 mg and about 200 mg per day. In managing the subject, the therapy should be initiated at a lower dose, perhaps about 1 mg to about 25 mg, and increased if necessary up to about 200 mg to about 1000 mg per day as either a single dose or divided doses, depending on the subject's global response. It may be necessary to use dosages of the active ingredient outside the ranges disclosed herein in some cases, as will be apparent to those of ordinary skill in the art. Furthermore, it is noted that the dietitian, clinician or treating physician will know how and when to interrupt, adjust, or terminate therapy in conjunction with individual patient responses and conditions, as will be readily known by those of ordinary skill in the art.

In some embodiments, the amount of total ginsenoside administered to a subject in a method as provided herein is about 5 µg/kg, about 50 µg/kg, about 100 µg/kg, about 150 µg/kg, about 250 µg/kg, about 500 µg/kg, about 1 mg/kg, about 5 mg/kg, about 10 mg/kg, about 25 mg/kg, about 50 mg/kg, about 75 mg/kg, about 100 mg/kg or more. In some embodiments, the dosage of total ginsenoside administered is about 0.01 mg to about 10 mg, about 0.1 mg to about 30 mg, about 0.5 mg to about 50 mg, about 1.0 mg to about 60 mg, about 5.0 mg to about 80 mg, or about 10 mg to about 100 mg, per kilogram of the subject's body weight per day.

In certain embodiments the ginsenoside will be administered to the subject about 10 min, about 20 min, about 40 min, about 1 h, about 2 h, about 3 h, about 10 h, about 12 h or about 24 h prior to being exposed to an elevated level of aldehyde due, but not limited, to ethyl alcohol ingestion.

In certain embodiments the ginsenoside will be administered to the subject at the same time when the event causing elevated aldehyde concentration, such as, for example, ethyl alcohol consumption, occurs.

In certain embodiments the ginsenoside will be administered to the subject about 10 min, about 20 min, about 40 min, about 1 h, about 2 h, about 3 h, about 6 h or about 12 h after being exposed to an elevated level of aldehyde due, but not limited, to ethyl alcohol ingestion.

In one embodiment the administration schedule of the ginsenoside comprises single or repeated administration according to the needs of the subject as determined by the skilled artisan.

In certain embodiments a combination of ginsenoside and glutamine are administered to a subject. Amounts of glutamine to be administered to the subject typically range, for example, from about 50 milligrams to about 3 grams, from about 150 milligrams to about 1.5 grams, from about 400 milligrams to about 2 grams, more typically about 900 milligrams to about 1.2 grams or about 1 gram of glutamine per day.

In embodiments where a combination of ginsenoside and silymarin are administered to a subject, typically about 20 milligrams to about 800 milligrams, more typically about 100 milligrams to about 600 milligrams or about 400 grams of silymarin are administered to the subject per day.

In one embodiment the subject experiencing an elevated acetaldehyde level has been exposed to acetaldehyde from environmental sources, such as a wood burning fire, tobacco smoke, automobile or diesel exhaust.

In one embodiment the subject experiencing an elevated acetaldehyde level is a carrier of a compromised aldehyde dehydrogenase.

In one embodiment the subject experiencing an elevated acetaldehyde level has been consuming ethyl alcohol.

8. EXAMPLES

8.1. Alcohol Dehydrogenase (ADH) Activity

This example demonstrates that some but not all ginsenosides decrease the catalytic activity of alcohol dehydrogenase (ADH). In particular, protopanaxadiol type ginsenosides were found to decrease ADH activity whereas protopanaxatriol type ginsenosides had no significant effect on ADH activity.

Ginsenosides Rb1, Rb2, Rc, Rd, Re and Rg1 were obtained from ChromaDex Inc., Irvine, Calif., USA. The ginsenosides were dissolved in DMSO to prepare a stock solution. Prior to performing an activity assay, portions of a ginsenosides stock solution were diluted in aqueous reaction buffer solution and from which samples were taken and assayed for activity.

ADH activity was measured in a colorimetric assay as described in Gibla and Gonzalex-Durante, J. Biochem. Biophys. Methods 1993, 26, 87-93, the contents of which are incorporated by reference herein in its entirety.

Results provided in FIG. 1 show the effects of individual ginsenosides Rb1, Rb2, Rc, Rd, Re and Rg1 on ADH activity. FIG. 2 provides a comparison of the averaged effects of protopanaxadiols Rb1, Rb2, Rc and Rd versus the averaged effects of protopanaxatriols Re and Rg1. These results demonstrate that concentrations greater than about 50 µg/mL of a protopanaxadiol type of ginsenoside reduce the activity of ADH. In particular, ginsenosides Rb1, Rb2, Rc and Rd reduced ADH activity and the protopanaxatriol type ginsenosides Re and Rg1 did not have a significant effect on ADH activity (FIG. 1). The average decrease in ADH activity by protopanaxadiols as compared to protopanaxatriols was >20% (FIG. 2).

8.2. Aldehyde Dehydrogenase (ALDH) Activity Assay

This example demonstrates that some but not all ginsenosides increase the catalytic activity of ALDH. In particular, protopanaxadiol type ginsenosides were found to increase ALDH activity whereas protopanaxatriol type ginsenosides had no significant effect on ALDH activity.

Stock solutions of ginsenosides Rb1, Rb2, Rc, Rd, Re and Rg1 in DMSO as described above, were prepared. ALDH was obtained from Sigma-Aldrich (product no. A 6338). Enzyme activity assays were performed in vitro according to instructions supplied by the vendor as modified by the addition of test substances, which is based on assay described in Bostian et al., Biochemical Journal 1978, 173, 773-786, the contents of which are incorporated by reference herein in their entirety. This assay measures the conversion of acetaldehyde into acetic acid via reduction by ALDH catalysis.

Results provided in FIG. 3 show the effects of individual ginsenosides Rb1, Rb2, Rc, Rd, Re and Rg1 on ALDH activity. FIG. 4 provides a comparison of the averaged effects of protopanaxadiols Rb1, Rb2, Rc and Rd versus the averaged effects of protopanaxatriols Re and Rg1. These results demonstrate that concentrations greater than about 5 µg/mL of a protopanaxadiol type ginsenoside increases the activity of ALDH. In particular, ginsenosides Rb1, Rb2, Rc and Rd increased ALDH activity and protopanaxatriol ginsenosides Re and Rg1 did not have a significant effect on ALDH activity (FIG. 3). The average increase in ALDH activity by protopanaxadiols as compared to protopanaxatriols was >50% (FIG. 4).

8.3. Exemplary Ginsenoside Compositions

This example describes the preparation of different ginsenoside nutraceutical compositions.

Preparation of Capsule Compositions

Example A

Ginsenoside composition 500 mg (Rb1 165 mg, Rb2 40 mg, Rc 250 mg, Rd 45 mg), Lactose 50 mg, Starch 50 mg, Talc 2 mg, and Magnesium Stearate in proper quantity. The above-mentioned ingredients are mixed, and filled in a gelatin capsule according to conventional preparation for capsules known to those skilled in the art to give a capsule.

Example B

Ginsenoside (such as Rb1 35 mg), Lactose 50 mg, Starch 50 mg, Talc 2 mg, and Magnesium Stearate in proper quantity. The above-mentioned ingredients are mixed, and filled in a gelatin capsule according to conventional preparation for capsules known to those skilled in the art to give a capsule.

Example C

Ginsenoside (such as Rb2 10 mg), Lactose 50 mg Starch 50 mg Talc 2 mg, and Magnesium Stearate proper quantity. The above-mentioned ingredients are mixed, and filled in a gelatin capsule according to conventional preparation for capsules known to those skilled in the art to give a capsule.

Example D

Ginsenoside composition 100 mg (Rb1 25 mg, Rb2 25 mg, Rc 25 mg, Rd 25 mg), Glutamine 400 mg, Lactose 50 mg, Starch 50 mg, Talc 2 mg, and Magnesium Stearate in proper quantity. The above-mentioned ingredients are mixed, and filled in a gelatin capsule according to conventional preparation for capsules known to those skilled in the art to give a capsule.

Example E

Ginsenoside (such as Rb1 35 mg), Glutamine 400 mg, Lactose 50 mg, Starch 50 mg, Talc 2 mg, and Magnesium Stearate in proper quantity. The above-mentioned ingredients are mixed, and filled in a gelatin capsule according to conventional preparation for capsules known to those skilled in the art to give a capsule.

Example F

Ginsenoside (such as Rb2 10 mg), Silymarin 200 mg, Lactose 50 mg Starch 50 mg Talc 2 mg, and Magnesium Stearate proper quantity. The above-mentioned ingredients are mixed, and filled in a gelatin capsule according to conventional preparation for capsules known to those skilled in the art to give a capsule.

Example G

Ginsenoside composition 300 mg (Rb1 75 mg, Rb2 75 mg, Rc 75 mg, Rd 75 mg), Silymarin 200 mg, Lactose 50 mg, Starch 50 mg, Talc 2 mg, and Magnesium Stearate in proper quantity. The above-mentioned ingredients are mixed, and filled in a gelatin capsule according to conventional preparation for capsules known to those skilled in the art to give a capsule.

8.4. Reducing Acetaldehyde Concentration in a Subject

The examples below will demonstrate that ginsenosides can prevent or alleviate symptoms associated with ethyl alcohol intolerance in human subjects.

8.4.1. Study No. 1

This example will demonstrate that the peak acetaldehyde concentration in the blood due to drinking ethyl alcohol can be reduced in a subject after being administered a ginsenoside relative to the peak concentration in the subject after drinking ethyl alcohol in the absence of the ginsenoside.

Techniques for blood sampling and analysis of acetaldehyde levels in blood are well known to those of skill in the art. See, e.g., Inoue et al., *Alcoholism: Clincical and Experimental Research* 1984, 8, 319-322; Stowell, *Clin. Chim. Acta.* 1979, 98, 201-5; and Chen et al., *Alcoholism: Clinical and Experimental Research* 1995, 19, 939-944, each incorporated herein by reference in its entirety. Also, those skilled in the art are aware that increases in acetaldehyde levels in a subject will increase the subject's heart rate, and that heart rate can be used as indicator of acetaldehyde levels. Maximal concentrations of acetaldehyde accumulation typically follow fifteen minutes to one hour following ethanol consumption in a subject with ethyl alcohol intolerance, for example, due to reduced or absent ALDH2 activity.

Human subjects known to have intolerance to ethyl alcohol are identified and randomly placed into treatment (ginsenoside and ethyl alcohol) and control (placebo and ethyl alcohol) groups. Heart rates and blood samples are drawn from each subject at times prior to, and after administration, of ginsenoside or placebo and ethyl alcohol. Protopanaxadiol ginsenoside in the form of a liquid composition is orally administered in a 0.8 mg ginsenoside/kg body weight dose to the treatment group and a placebo is administered to the control group. Thirty minutes after administration of ginsenoside or placebo, ethyl alcohol (0.5 g/kg) is administered to each subject. Periodically heart rate will be monitored and blood samples withdrawn over time course of up to six hours. Subjects can also be asked to self-report symptoms such as headaches, dizziness, etc., and can be evaluated for flushing and/or other symptoms. Approximately one week later the experiment is repeated on the same subjects but the treatments are switched, that is, subjects formerly in the control group will be the treatment group and vice versa for the subjects formerly in the treatment group.

Data pertaining to the heart rates, acetaldehyde concentrations, and so forth, from the subjects of each group are compared.

8.4.2. Study No. 2

As explained above, certain individuals are sensitive to the effects of ethyl alcohol, which will elicit symptoms such as facial flushing and increased heart rate in such individuals when consumed in modest amounts that would not normally trigger such symptoms in others of the larger general population of people. This study will demonstrate that the severity of the facial flushing and increases in heart rate can be attenuated in individuals that have a history of exhibiting such symptoms to modest amounts of alcohol by the administration of a ginsenoside composition as provided herein. Individuals with a history of flushing are selected as subjects for participation in the study described below.

Ginsenoside composition: A *ginseng* extract having a 30% total ginsenoside fraction was prepared in powdered form and encapsulated (25 mg extract per capsule). The ratio of the protopanaxadiol to protopanaxatriol type of ginsenosides in the ginsenoside fraction was about 60:40. The ginsenoside composition preparation used in this study is considered to be generally recognized as safe (GRAS).

The study is self-conducted by each subject according to the following protocol.

Step A1: Establish Baseline Alcohol Tolerability a) The subject records his or her pulse at rest while sitting before drinking any alcohol. The subject should not take any caffeine, pseudoephedrine, blood pressure medications, or any other medications known to alter heart rate for at least 24 hours prior to this baseline measure, and no solid food for at least 4 hours prior to this baseline measure. The subject should have a family member or friend judge "redness," and take a facial photograph of the subject for pre-drinking baseline. The subject should also evaluate his or her facial flushing.

b) The subject drinks 6 oz white wine (11 to 12.5% alcohol content—no dessert wines) within ≦30 min as tolerated, or until at least two of the following events occurred and/or the subject cannot tolerate any more alcohol:
  i. Sitting HR (heart rate) at rest increased by at least 30 beats/min (monitor your heart rate every 15 minutes during the 30 minute drinking period);
  ii. Facial flush score of ≧3+;
  iii. Experience 1 or more symptoms associated with acetaldehyde exposure such as headache, moderate dizziness, nausea, vomiting.

c) The subject may repeat drinking another 3 oz of white wine every 20 minutes if none of the above events occurs, not to exceed a total of 12 oz (including the first 6 oz). Continue study participation to steps G2 and G4 only if at least one of the above symptoms occurred with alcohol intake.

d) Have a photograph taken under the identical lighting condition and with the same background as in step A1, part a, above.

e) Record the amount of alcohol consumed and the time of consumption.

f) Measure heart rate and monitor flushing every 15 min for four hours after completion of alcohol intake or until both return to normal (pre-drinking baseline). Record the time when heart rate and flushing to return to pre-drinking baseline values.

Step G2: Test on 50 Milligram Ginsenoside Composition
Step G2 is to be performed at least 3 days after step A was completed.

a) The subject records his or her pulse at rest while sitting before drinking any alcohol. The subject should not take any caffeine, pseudoephedrine, blood pressure medications, or any other medications known to alter heart rate for at least 24 hours, and no solid foods for at least 4 hours, prior to anticipated alcohol intake time. The subject should have a family member or friend judge "redness," and take a facial photograph of the subject for pre-drinking baseline. The subject should also evaluate his or her own facial flushing.

b) Take 2 capsules of the ginsenoside composition.

c) After 1.5 hours from taking the ginsenoside composition, the subject should perform the following:
  i. Take his or her pulse at rest while sitting just before drinking any alcohol;
  ii. Ask the family member or friend to judge "redness", and self-evaluate facial flushing. Take a facial photograph for pre-drinking baseline. (The lighting condition for all photographs throughout the study should be the same.)
  iii. Drink the same amount of the identical white wine as in step A1, part b, above, and record the time of alcohol intake.

Measure heart rate and monitor flushing every 15 min for four hours following alcohol intake or until both heart rate and flushing has return to normal (pre-drinking baseline). Record the time when heart rate and flushing to return to pre-drinking baseline values.

Step G4: Test on 100 Milligram Ginsenoside Composition
Step G4 is to be performed at least 3 days after step G2 was completed.

a) The subject records his or her pulse at rest while sitting before drinking any alcohol. The subject should not take any caffeine, pseudoephedrine, blood pressure medications, or any other medications known to alter heart rate for at least 24 hours, and no solid foods for at least 4 hours, prior to anticipated alcohol intake time. The subject should have a family member or friend judge "redness," and take a facial photograph of the subject for pre-drinking baseline. The subject should also evaluate his or her own facial flushing.

b) Take 4 capsules of the ginsenoside composition.

c) After 1.5 hours from taking the ginsenoside composition, the subject should perform the following:
  i. Take his or her pulse at rest while sitting just before drinking any alcohol;
  ii. Ask the family member or friend to judge "redness", and self-evaluate facial flushing. Take a facial photograph for pre-drinking baseline. (The lighting condition for all photographs throughout the study should be the same.)
  iii. Drink the same amount of the identical white wine as in step A1, part b, above, and record the time of alcohol intake.

Measure heart rate and monitor flushing every 15 min for four hours following alcohol intake or until both heart rate and flushing has return to normal (pre-drinking baseline). Record the time when heart rate and flushing to return to pre-drinking baseline values.

Results: Two subjects completed the step A1 and at least one of steps G2 and G4 of the study no. 2 protocol described above. Subject 1, a 46 year old female with a self-reported history of severe flushing response when drinking alcohol. Subject 1 describes herself as typically abstaining from alcohol. Subject 1 performed steps A1 and G4 as described above. Heart rate and evaluation of flushing in response to drinking alcohol are as reported in Table 1.

TABLE 1

Results for Subject 1 (P.Y.)

| Time (min) | Baseline (Step A1) | | Ginsenoside (Step G4) | |
|---|---|---|---|---|
| | Heart rate (bpm) | Flushing | Heart rate (bpm) | Flushing |
| 0 | 64 | | 64 | |
| 15 | 92 | 2 | 84 | 1 |
| 30 | 120 | 3 | 88 | 2 |
| 45 | 104 | 3 | 92 | 3 |
| 60 | | 3 | 92 | 3 |
| 75 | 108 | | 80 | 3 |
| 90 | 84 | | 80 | 3 |
| 105 | 76 | 2 | 80 | 2 |
| 120 | 84 | 2 | 80 | 2 |
| 135 | 80 | 1 | 88 | 2 |
| 150 | 88 | 1 | 80 | |
| 165 | 84 | 1 | | |
| 180 | 88 | 1 | 76 | 2 |
| 210 | | | 76 | 1 |
| 240 | | | | |
| 270 | | | | |
| 300 | 80 | 0 | 72 | 1 |
| 330 | | | | |
| 360 | | | 64 | |
| average | 89 | 1.7 | 80 | 2.1 |

After taking the ginsenoside composition prior to drinking alcohol, subject 1 reported that, after drinking ethyl alcohol, she felt better when taking a ginsenoside composition than without the ginsenoside composition. She reported that the flushing she experiences when drinking alcohol took longer to manifest when she took the ginsenoside composition (Table 1). As shown in FIG. 5A, subject 1's peak heart rate in response to the alcohol was much lower after taking the ginsenoside composition (circles) than when drinking the equivalent amount of alcohol in absence of the ginsenoside composition (solid squares).

Subject 2, is a 23 year old male with a self reported history of flushing response when drinking alcohol. Subject 2 describes himself as occasionally drinking small amounts of alcohol. Subject 2 performed steps A1 and G2 as described above. Heart rate and evaluation of flushing in response to drinking alcohol are as reported in Table 2.

TABLE 2

Results for Subject 1 (B.)

| | Baseline (Step A1) | | Ginsenoside (Step G2) | |
|---|---|---|---|---|
| Time (min) | Heart rate (bpm) | Flushing | Heart rate (bpm) | Flushing |
| 0 | 80 | 0 | 79 | 0 |
| 15 | 94 | 0 | 94 | 0 |
| 35 | 99 | 1 | 99 | 1 |
| 50 | 102 | 2 | 95 | 1 |
| 75 | 128 | 2 | 109 | 1 |
| 90 | 128 | 3 | 115 | 2 |
| 110 | 133 | 3 | 109 | 2 |
| 130 | 123 | 3 | | |
| 145 | 139 | 2 | 126 | 1 |
| 185 | 117 | 2 | | |
| 205 | 86 | 1 | | |
| average | 112 | 1.7 | 103 | 1.0 |

After taking the ginsenoside composition prior to drinking alcohol, subject 2 reported experiencing a noticeable reduction in flushing that normally occurs when drinking alcohol in the absence of taking the ginsenoside composition (Table 1). As shown in FIG. 5B, Subject 2's peak heart rate in response to the alcohol was lower after taking the ginsenoside composition (circles) than when drinking the equivalent amount of alcohol in absence of the ginsenoside composition (solid squares).

These results demonstrate that a ginsenoside composition as provided herein can reduce symptoms, such as, for example, discomfort, flushing, and increased heart rate associated with alcohol sensitivity.

Although the foregoing invention has been described in some detail by way of illustration and example for purposes of clarity of understanding, it will be apparent to those skilled in the art that certain changes and modifications will be practiced. Therefore, the description and examples should not be construed as limiting the scope of the invention, which is delineated by the appended claims.

All publications and patent applications cited in this specification are herein incorporated by reference as if each individual publication or patent application were specifically and individually indicated to be incorporated by reference.

It is claimed:

1. A ginsenoside composition suitable for administration to a subject consisting of a non-ginsenoside fraction and a ginsenoside fraction, wherein the ginsenoside fraction consists of Rb1, Rb2, Rc and Rd.

2. The ginsenoside composition of claim 1, wherein the ginsenoside composition is a pharmaceutical composition and the non-ginsenoside fraction comprises a pharmaceutically acceptable carrier, excipient, diluent or solvent.

3. The ginsenoside composition of claim 1, wherein the ginsenoside composition is suitable for oral administration to a subject.

4. The ginsenoside composition of claim 1, wherein the ginsenoside composition is a nutraceutical composition and the non-ginsenoside fraction comprises a physiologically acceptable carrier, excipient, diluent or solvent.

5. The ginsenoside composition of claim 1 wherein the non-ginsenoside fraction further comprises glutamine or silymarin.

6. An article of manufacture comprising packaging material and a ginsenoside composition of claim 2.

7. A method for increasing the rate of reducing acetaldehyde concentration in a subject comprising
administering to a subject in need thereof an amount of the ginsenoside composition of claim 1 effective to increase the rate of reducing the acetaldehyde concentration in the subject relative to the rate of reducing the acetaldehyde concentration in the subject in the absence of the ginsenoside.

8. A method for preventing or ameliorating a symptom of elevated acetaldehyde concentration in a subject comprising
administering to a subject in need thereof an amount of the ginsenoside composition of claim 1 effective to prevent or ameliorate a symptom of elevated acetaldehyde concentration in the subject.

9. A method for reducing a risk in a subject for a disease or disorder caused by intake of ethyl alcohol comprising
administering to a subject in need thereof an amount of the ginsenoside composition of claim 1 effective to increase catabolism of acetaldehyde in the subject, wherein the acetaldehyde is a product of ethyl alcohol consumption by the subject and wherein increasing catabolism of acetaldehyde reduces a risk for a disease or disorder in the subject caused by intake of the ethyl alcohol.

10. The method of claim 7, wherein the subject is human.

11. The method of claim 7, wherein the subject has an altered ethyl alcohol metabolism.

12. The method of claim 11, wherein the subject has a reduced aldehyde dehydrogenase subtype 2 (ALDH2) activity.

13. The method of claim 7, wherein the acetaldehyde is a product of ethyl alcohol catabolism in the subject.

14. The method of claim 7, wherein the subject is exposed to acetaldehyde in cigarette smoke or in the environment outside of the subject.

15. The method of claim 8, wherein a symptom of elevated acetaldehyde concentration comprises flushing, elevated heart rate, palpitations, hypotension, nausea, dizziness, headache, vomiting, diarrhea, upset stomach, ataxia or confused consciousness.

16. The method of claim 9, wherein the disease or disorder comprises hangover, alcoholic gastritis or alcohol-induced liver damage.

17. The method of claim 9, wherein the disease or disorder comprises upper aerodigestive tract cancers, digestive tract cancers or breast cancer.

18. The method of claim 17, wherein the upper aerodigestive tract cancer comprises esophageal, oropharynx, hypopharynx, larynx, head or neck cancer.

19. The method of claim 17, wherein the digestive cancer comprises stomach or colon cancer.

20. The method of claim 9, wherein the disease or disorder comprises late-onset Alzheimers disease, hypertension, myocardial infarction, Parkinson's disease, amyotropic lateral sclerosis, and cerebral ischemia.

21. The method of claim 7, wherein the acetaldehyde concentration is in the blood, salvia and/or tissue of the subject.

22. The method of claim 7, wherein about 0.1 μg to about 100 mg ginsenoside per kilogram of the subject's body weight are administered per day.

23. The method of claim 22 further comprising administering about 400 milligrams to about 2 grams of glutamine to the subject per day.

24. The method of claim 22 further comprising administering about 20 milligrams to about 800 milligrams of silymarin to the subject per day.

* * * * *

UNITED STATES PATENT AND TRADEMARK OFFICE
CERTIFICATE OF CORRECTION

PATENT NO.         : 8,440,632 B2                                              Page 1 of 1
APPLICATION NO. : 12/863979
DATED              : May 14, 2013
INVENTOR(S)        : Daley et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 260 days.

Signed and Sealed this

Eighth Day of September, 2015

Michelle K. Lee
*Director of the United States Patent and Trademark Office*